United States Patent [19]

Brinkmeyer et al.

[11] Patent Number: 4,866,211
[45] Date of Patent: Sep. 12, 1989

[54] HYDROCARBON CONVERSION PROCESSES

[75] Inventors: Francis M. Brinkmeyer; Donald F. Rohr, Jr., both of Bartlesville, Okla.

[73] Assignee: Phillips Petroleum Company, Bartlesville, Okla.

[21] Appl. No.: 12,968

[22] Filed: Feb. 10, 1987

Related U.S. Application Data

[63] Continuation of Ser. No. 507,395, Jun. 24, 1983, abandoned.

[51] Int. Cl.$^4$ .............................................. C07C 41/06
[52] U.S. Cl. .................................. 568/697; 585/660; 585/670
[58] Field of Search ................. 568/697; 585/660, 670

[56] References Cited

U.S. PATENT DOCUMENTS

| | | |
|---|---|---|
| 2,363,824 | 11/1944 | Wolk . |
| 2,395,016 | 2/1946 | Schulze et al. . |
| 2,428,516 | 10/1947 | Drennan . |
| 3,485,887 | 12/1969 | Kronig et al. . |
| 3,632,525 | 1/1972 | Rausch ................................ 585/670 |
| 3,641,182 | 2/1972 | Box et al. ............................ 585/660 |
| 4,217,461 | 8/1980 | Ward . |
| 4,229,602 | 10/1980 | Brinkmeyer et al. . |
| 4,229,609 | 10/1980 | Hutson et al. . |
| 4,320,233 | 3/1982 | Makovec . |
| 4,408,085 | 10/1983 | Gottlieb et al. ..................... 568/697 |

FOREIGN PATENT DOCUMENTS 0042252 12/1981 European Pat. Off. ............ 568/697

OTHER PUBLICATIONS

Clementi et al., Hydrocarbon Processing, Dec. 1979, pp. 109-113.

*Primary Examiner*—Howard T. Mars
*Attorney, Agent, or Firm*—George E. Bogatie

[57] ABSTRACT

Steam active reforming catalyst is described which in addition to converting isoparaffins to isoolefins also isomerizes 1-olefins at least in part to internal olefins. In a combined steam active reforming and ether forming operation a 1-olefin containing stream can be recycled to the steam active reforming zone whereby this 1-olefin is converted to materials which in a separation step downstream from the ether forming reaction can be readily separated from the isoparaffin, the isolefin and the 1-olefin which are recycled to the steam active reforming zone. The steam active reforming catalyst thus has both the function of a reforming (dehydrogenation) catalyst and that of an isomerization catalyst for disposing of the 1-olefin byproduct and preventing its buildup in the operation.

3 Claims, 2 Drawing Sheets

HYDROCARBON CONVERSION PROCESSES

This application is a continuation of application Ser. No. 507,395, filed June 24, 1983 now abandoned.

This invention relates to the conversion of paraffins to olefins as well as to the conversion of 1-olefins to internal olefins. More specifically the invention relates to an olefin isomerization process. In another aspect the invention relates to a dehydrogenation process.

BACKGROUND OF THE INVENTION

The conversion of paraffins to olefins is a well known process widely researched and described in the prior art. U.S. Pat. No. 4,229,609 describes a process in which dehydrogenatable hydrocarbon is dehydrogenated using a bed of steam active dehydrogenation catalyst which is repetitively regenerated.

THE INVENTION

It is one object of this invention to provide a new dehydrogenation process.

Another object of this invention is to provide an integrated process for the production of dialkyl ethers.

Further objects, advantages, features, details and embodiments of this invention will become apparent to those skilled in the art from the following detailed description of the invention, the appended claims and the drawing in which FIG. 1 shows a schematic flow diagram for the production of dialkyl ether from paraffins and alcohol, and FIG. 2 shows a bar diagram of butene conversion products.

In accordance with this invention it has been discovered that a catalyst, which will be described in more detail in the following and which has been known to be an effective dehydrogenation catalyst, is also an excellent isomerization catalyst for converting 1-olefins to internal olefins.

Thus, in accordance with a first embodiment of this invention, a process for the conversion of 1-olefins to internal olefins is provided. This process comprises contacting a 1-olefin containing feedstream as defined and obtaining an effluent stream which is diminished in 1-olefin content and enriched in content of the corresponding internal olefin or olefins.

More specifically, 1-olefins having 4 to 10 carbon atoms can be converted by contacting these 1-olefins with the catalyst to be defined and under isomerization conditions.

Olefins which can be used in this first embodiment of this invention include butene-1, pentene-1, hexene-1, 4-methyl-1-pentene, 1-octene and 1-decene. The particularly preferred olefins are the normal alpha-olefins. Other olefins such as 2,3-dimethyl-1-butene can, however, also be used.

The isomerization conditions employed in this first embodiment of this invention are preferably in the following ranges:

ISOMERIZATION CONDITIONS

|  | Generally Employed | Preferably Employed |
| --- | --- | --- |
| Temperature (°F.) | 950–1150 | 1080–1120 |
| Pressure (psig) | 0–200 | 0–100 |
| Steam to Hydrocarbon (molar ratio) | 1/1–25/1 | 2/1–15/1 |
| LHSV* | 1–15 | 1.5–10 |
| Hydrogen to Hydrocarbon** (molar ratio) | 0–1.3/1 | 0–0.8/1 |

*Liquid Hourly Space Velocity of hydrocarbon, i.e. volume of hydrocarbon per volume of catalyst per hour.
**In isomerization and dehydrogenation $H_2$ addition is not used.

Catalyst

The catalyst utilized in all of the embodiments of this invention is broadly a Group VIII metal catalyst on a support. The preferred Group VIII metal is platinum. The support can be alumina, silica, magnesia, zirconia, alumina-silicates, Group II aluminate spinels and mixtures of such supports. Group VIII metals are those classified in Group VIII in the Periodic Table of the Elements as set forth in *Chemical Rubber Companies,* "Handbook of Chemistry and Physics", 45th Edition (1964) page B-2.

The amount of Group VIII metal is not critical. Generally any amount resulting in catalytic activity of the support/metal combination can be utilized. Typically the Group VIII metal is present in the catalyst in amount in the range of about 0.01 to about 10 parts by weight per 100 parts by weight of support, and frequently the quantity is in the range of about 0.1 to about 5 parts by weight.

Co-promoter metals can be employed in the catalyst in conjunction with the Group VIII metal. The preferred co-promoters are lead, tin and germanium, generally employed in a quantity up to 10, preferably 5, parts by weight per 100 parts by weight of the support. The co-promoter when employed will be typically used in the range of 0.01 to 10 parts by weight and frequently in a range of 0.1 to 1 parts by weight of co-promoter per 100 parts by weight of support. The co-promoter metals can be employed as chemical compounds such as halides, nitrates, oxylates, acetates, carbonates, propionates, tartrates, bromates, chlorates, oxides, hydroxides, etc. Among the co-promoters, tin is the preferred metal and conveniently and effectively stannous halides can be utilized.

The catalyst used in the processes of this invention are obtained by known methods such as impregnation of the support with the metal compounds. The compounds employed should be such that upon calcination of the catalyst no significant amount of extraneous material remains on the catalyst, particularly no further metals which would interfere with the catalytic process envisaged.

The preferred catalyst useful in the processes of this invention is a catalyst comprising platinum on zinc aluminate, particularly and preferably zinc aluminate spinel. Most preferably the catalyst is co-promoted with tin. Thus, the most preferred catalyst of this invention consists essentially of zinc aluminate spinel, platinum and tin. One typical catalyst can contain about 0.1 to about 5 parts by weight of platinum and about 0.1 to 1 parts by weight of tin on 100 parts by weight of a zinc aluminate spinel support. The preferred catalyst has a pore volume in the range of 0.23–0.55 cc/g and surface area in the range of 12–30 m²/g.

Ether Production

A second embodiment of this invention resides in a process to produce ethers from paraffins. In accordance with this second embodiment, an isoparaffin containing stream is passed into contact with a reforming catalyst, which is the catalyst as defined above, in an isomerization and reforming zone to convert at least some of the isoparaffin to isoolefin. A reaction effluent is withdrawn from the isomerization and reforming zone. At least a portion of this reaction effluent is passed into an ether forming zone, and the isoolefin is reacted with an alcohol in this ether forming zone to form an ether. From the ether forming zone an ether containing effluent is withdrawn, and this ether containing effluent also contains 1-olefin and corresponding internal olefin as well as unreacted isoparaffin. The ether containing effluent is separated into an ether product stream, a 1-olefin containing stream which also contains a substantial amount of the unreacted isoparaffin and an internal olefin containing stream. This internal olefin is then withdrawn from the internal olefin containing stream. In accordance with this invention the 1-olefin containing stream is then recycled into the isomerization and refining zone and into contact with the catalyst such as to convert at least a portion of the 1-olefin into a corresponding internal olefin.

In a typical ether reaction such as a reaction to form methyl tertiary butyl ether an isoolefin is reacted with an alcohol. These processes are well known in the art and have been widely described in a variety of environments. Unreacted isobutane (after ether removal) could be recycled to a reforming operation to convert the isobutane to isobutylene. The problem with such an operation is, however, that other hydrocarbons which are closely boiling will also be recycled so that these hydrocarbons which do not react in the ether forming reaction will rapidly build up in such a loop to an intolerable level. While fractionation could be used to remove for instance butene-2's, the butene-1 cannot be effectively removed because its boiling point is very close to that of isobutene.

It has now been discovered, however, in accordance with this invention that recycling of butene-1 to the reforming reaction (the catalytic reaction in which isobutane is converted to isobutene) does not result in such a buildup because the butene-1 is converted under the reforming conditions to butene-2's; these butene-2's can be readily removed by fractionation from any unreacted isobutane and isobutene. Therefore in accordance with this invention the catalyst as described and defined above has a dual function: it acts in the normal dehydrogenation fashion to convert isobutane to isobutene, and it also acts as a isomerization catalyst to convert butene-1 into butene-2's. The reforming zone is therefore both a reforming and isomerization zone and the catalyst acts both as a catalyst to produce the desired product, isobutene, which is converted into the ether and as a byproduct disposal catalyst by converting butene-1 into butene-2's.

The isomerization and reforming conditions employed in the steam active reaction zone are the same as those described above in connection with the first embodiment of this invention. Specifically, the following conditions are typically and preferably employed:

Reforming and Isomerization Conditions

|  | Generally Employed | Preferably Employed |
|---|---|---|
| Temperature (°F.) | 950–1150 | 1080–1120 |
| Pressure (psig) | 0–200 | 0–100 |
| Steam to Hydrocarbon (molar ratio) | 1/1–25/1 | 2/1–15/1 |
| LHSV* | 1–10 | 1.5–8 |

*Liquid Hourly Space Velocity of hydrocarbon, i.e. volume of hydrocarbon per volume of catalyst per hour.

The catalyst utilized in this embodiment as well as the preferred catalyst is the same as that described above.

The ether forming reaction step of this invention is as such a known step. The reaction is that of an isoolefin with an alcohol. Typical ether forming conditions are given in the following table.

Ether Forming Conditions

|  | Generally Employed | Preferably Employed |
|---|---|---|
| Temperature (°F.) | 90–200 | 100–170 |
| Pressure (psig) | 40–600 | 85–260* |
| LHSV** | 0.2–30 | 0.5–20 |
| Isoolefin/Alcohol (mole ratio) | 0.2–2 | 0.8–1.3 |

*The pressure will be sufficient to maintain the reactants in the liquid phase.
**Liquid Hourly Space Velocity, volume of hydrocarbon per volume of catalyst per hour.

The catalyst employed in the ether forming reaction is also a conventional ether forming catalyst. Such ether forming catalyst have been described in U.S. Pat. Nos. 3,979,461 and 3,902,870. Specific examples are hydrogen fluoride, sulfuric acid, $AlCl_3$, as well as acidic ion exchange resins.

The main feedstock used for the process to produce an ether is an isoolefin produced from an isoparaffin having 4 to 8 carbon atoms. Isobutane is a particular example and a presently preferred material in view of the fact that methyl tertiary butyl ether is a high octane gasoline blending stock. Typical alcohols used in the ether forming reaction are alkanols having 1 to 3 carbon atoms. Methanol, in view of its availability, is presently preferred.

In the embodiment of this invention where the 1-olefin containing stream is introduced into contact with the reforming catalyst to achieve both a dehydrogenation of the isoparaffin producing isoolefin feedstock for the ether forming reaction and isomerization of the 1-olefin to internal olefins permitting ready removal of the 1-olefin which would otherwise build up in such a loop, the ratio of total isoparaffin to total 1-olefin will generally and preferably be as described in the following table.

TABLE

|  | Generally Employed | Preferably Employed |
|---|---|---|
| 1-olefin[1]/isoparaffin[2] (mole ratio) | 1/10 to 1/10000 | 1/100 to 1/1000 |

[1] The 1-olefin contained in the 1-olefin containing stream removed from the ether forming reaction effluent.
[2] Total isoparaffin including isoparaffin feedstock and unreacted isoparaffin in the 1-olefin containing stream from the ether forming reaction.

BRIEF DESCRIPTION OF THE DRAWING

Further details and preferred embodiments of this invention will be become apparent from the following description of the drawing and the specific examples.

In the drawing a schematic flow diagram for the process of this invention is shown. Into a steam active reformer 1 containing steam active reforming catalyst a feedstream comprising predominantly isobutane is introduced via line 2. Steam is introduced into the reformer 1 via line 3. The effluent from the steam active reformer is passed via line 11 to an MTBE reactor and separation system 4. Into this MTBE reactor and separation system 4 also a stream of methanol is introduced via line 5. Methyl tertiary butyl ether (MTBE) is withdrawn from the MTBE reactor and separation system 4 via line 6. A byproduct stream containing unreacted isobutane, unreacted isobutene, butene-1, butene-2, and n-butane is passed via line 7 into a fractionation tower 8. This fractionator 8 is operated under conditions to remove at least a major portion of butene-2, n-butane or heavier from the overhead stream. The overhead stream consisting essentially of butene-1, isobutane and isobutene is passed via line 9 back into the steam active reformer 1. The bottom stream containing butene-2 and n-butane as well as other byproducts is removed from the fractionator 8 via line 10.

Figure 1:
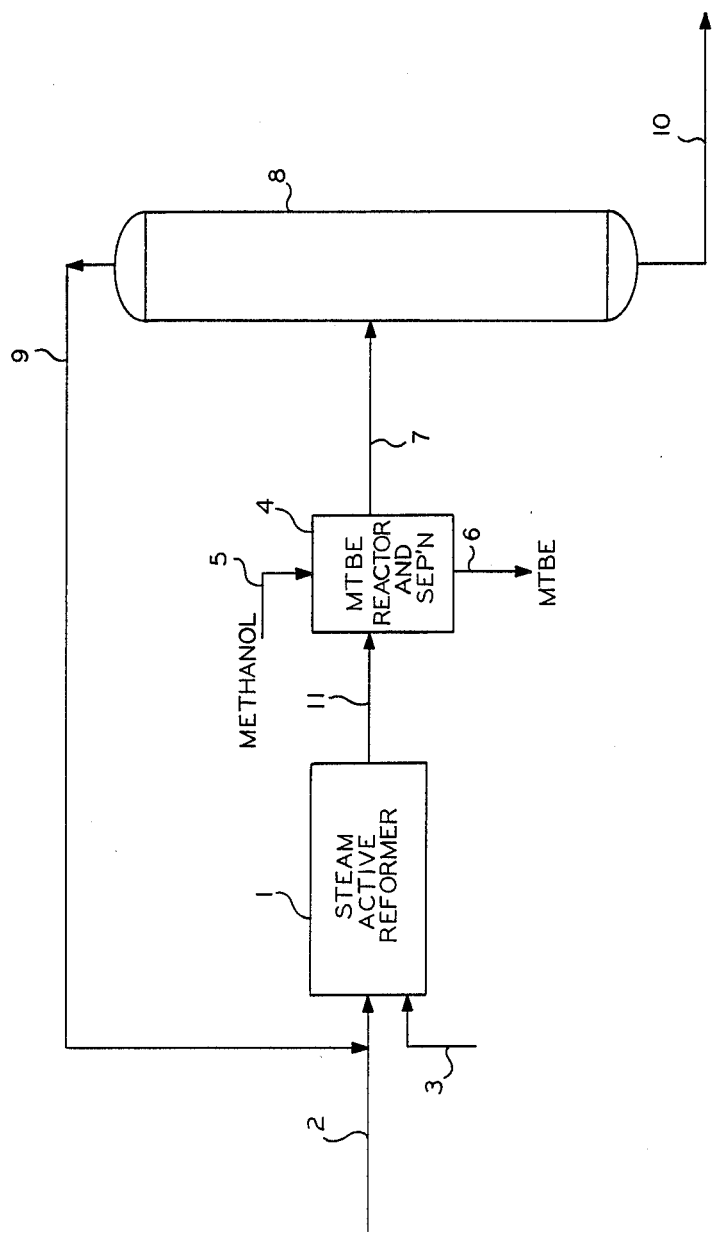

The butene-1 contained in the overhead stream 9 is converted in the steam active reformer 1 into butene-2's in an amount dictated by equilibrium to prevent any buildup of butene-1 in the loop containing line 9. The isobutane in the stream in line 9 is at least partially converted into isobutene in the steam active reformer 1 while isobutene is at least partially converted into the MTBE in the MTBE reactor and separation system 4. Thus the steam active reformer 1 in accordance with this invention has a dual function of being both a reformer and a byproduct disposal unit in which the butene-1 is converted to internal olefins, namely in this case, butene-2's which are removed as a bottoms stream from the fractionator 8.

EXAMPLE 1

A butene-1 stream was subjected in this example to steam active reforming conditions in contact with the steam active reforming catalyst. The feedstock composition as well as the reactor effluent composition are shown below in the table. This example was conducted at a 4.0 LHSV, 6/1 steam/hydrocarbon ratio, 50 psig system pressure, and an average bed temperature of 1050 F. The reactor was packed with ⅛ inch pellets of the preferred catalyst. The catalyst for this example contained 0.6 parts by weight of platinum, 1.0 parts by weight of tin, and 98.4 parts by weight of a zinc aluminate spinel support. The pore volume was 0.29 cc/g and surface area was 16 m$^2$/g. The catalyst bed had the dimensions of 2 inches in diameter by 14 inches in length and was charged with 900 grams of the preferred catalyst. The reactor feed and reactor effluent shown in the table was measured using a calibrated gas chromatograph. The analysis from the gas chromatograph is shown.

TABLE

| | Mole % | |
|---|---|---|
| | Reactor Feed | Reactor Effluent |
| $C_5^+$ | | 0.138 |
| $C_2$'s | | 0.590 |
| $CO_2$ | | 7.351 |
| $C_3$ | | 0.496 |
| $C_3^=$ | | 1.570 |
| $C_4$ | 0.245 | 0.066 |
| $nC_4$ | 0.047 | 7.725 |
| $C_4^{=1}$ | 99.032 | 14.793 |
| trans-$C_4^{=2}$ | 0.125 | 16.914 |
| cis-$C_4^{=2}$ | | 13.130 |
| butadiene | | 6.851 |
| $H_2$ | | 25.526 |
| $O_2$ | 0.085 | — |
| $N_2$ | 0.466 | 0.967 |
| methane | | 3.682 |
| CO | | 0.200 |

The above table shows that the steam active reforming catalyst is an effective isomerization catalyst converting a substantial amount of the 1-butene into 2-butenes. Because the 2-butenes boil substantially higher than isobutane, isobutene and 1-butene they can be readily removed from the ether forming reaction effluent in the process of this invention.

EXAMPLE 2

To determine the influence of isobutene recycle to the steam active reforming step as well as of the influence of recycled butene-1 to the steam active reforming step, the following two runs have been carried out.

In the first run a 95 mole percent isobutane feedstock was spiked with 5 mole percent isobutene. This mixture was fed to a steam active reforming pilot plant. As expected, the resulting conversions fell 1 to 3 percent below the conversions obtained with a pure feedstock. Various runs were carried at a liquid hourly space velocity of 4 and at a ratio of steam to hydrocarbon of 5:1. The average bed temperature as well as the conversion of isobutane is shown in the following tables together with the effects of 5 percent isobutene in an isobutane feed to a steam active reforming operation for various conversions of isobutane. These data are also based on a liquid hourly space velocity of 4 and a 5:1 steam to hydrocarbon mole ratio.

TABLE

| | % Isobutane Converted | |
|---|---|---|
| Temperature °F. | with no isobutene in feed | with 5% isobutene in feed |
| 1020 | 43.3 | 41.2 |
| 1040 | 46.9 | 44.8 |
| 1060 | 50.4 | 48.0 |
| 1080 | 53.9 | 51.6 |

| | % Selectivity to Isobutene | |
|---|---|---|
| Conversion of Isobutane % of Fresh Feed | with no isobutene in feed | with 5% isobutene in feed* |
| 42 | 95.7 | 94.4 |
| 44 | 95.1 | 93.8 |
| 46 | 94.5 | 93.3 |
| 48 | 93.9 | 92.6 |
| 50 | 93.3 | 92.1 |

*Selectivity computation: sel(%) = (isobutene in product − isobutene in feed) ÷ isobutane converted; thus "selectivity" is expected to be lowered.

A further run was carried out to determine the influence of recycling butene-1 together with isobutane into a steam active reforming operation. In this series of runs, 5 mole percent butene-1 was used in conjunction with 95 mole percent of isobutane as a feedstock in the same pilot plant operation described above. The following table shows the results obtained comparing the pure feedstock, i.e. pure isobutane with the spiked feedstock, i.e. the feedstock containing 95 mole percent isobutane and 5 mole percent butene-1. The data in this table are based on a liquid hourly space velocity of 4, a steam to hydrocarbon ratio of 5:1, a average bed temperature of 1050° F.

The following table shows the conversion of isobutane obtained with a pure feedstock as compared to a feedstock being spiked with 5 mole percent butene-1 as described for varying average bed temperatures.

TABLE

| Temperature °F. | % Isobutane Converted | |
|---|---|---|
| | with no butene-1 in feed | with 5% butene-1 in feed |
| 1048 | 48.4 | — |
| 1050 | — | 49.7 |
| 1054 | 48.8 | — |
| 1067 | 52.2 | — |
| 1070 | — | 51.0 |
| 1071 | 50.8 | — |
| 1074 | 51.8 | — |

The above results show that the steam active reforming operation can be effectively utilized to achieve both the regular steam active reforming, i.e. the conversion of an isoparaffin to an isoolefin and an isomerization operation, i.e. a conversion of butene-1 into butene-2's. It should be noted that some of the butene-1 is also being rehydrogenated back to normal butane. The isobutane feed to the reforming section contains a small amount of n-butane ranging from 0.5 mol % to 5 mol % n-butane. Normal butane can, however, be readily removed from isobutylene, isobutane and butene-1 in view of its higher boiling point.

EXAMPLE 3

Figure 2:
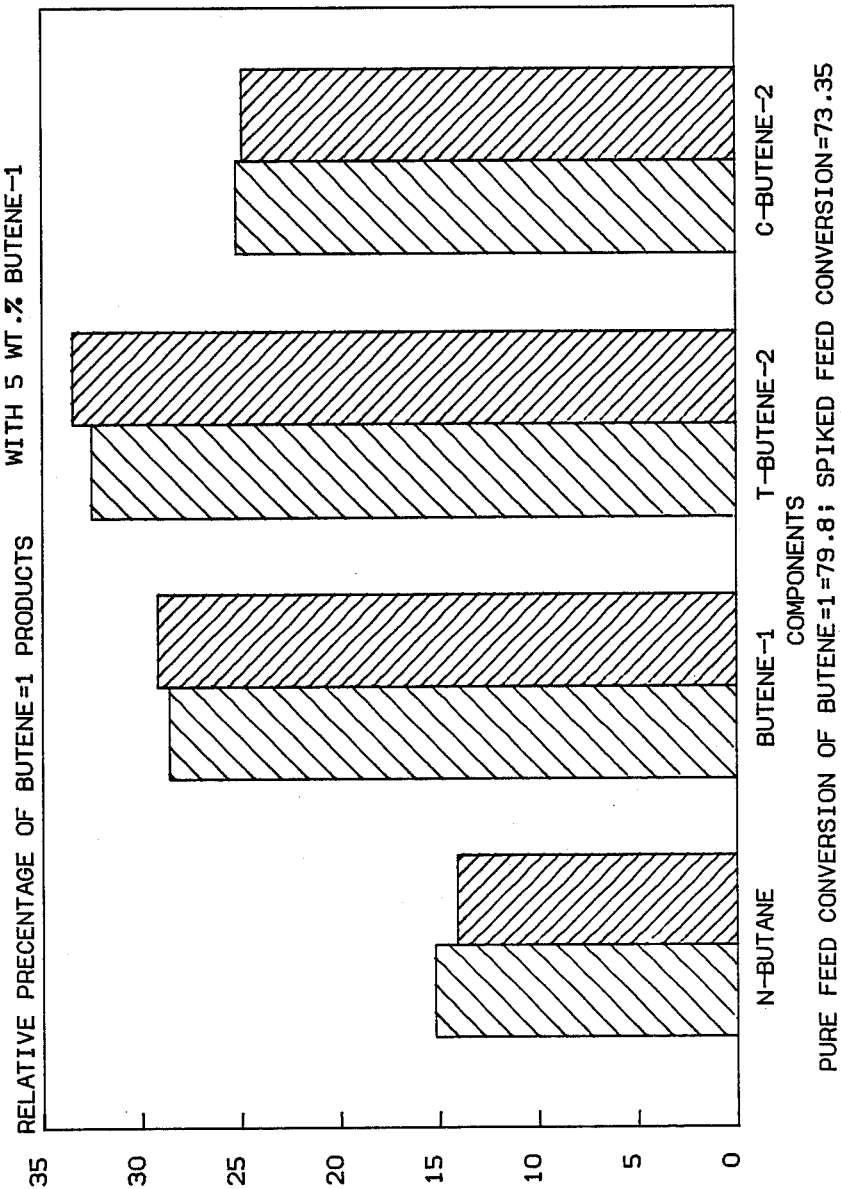

Comparative runs were carried out using the same catalyst and the conditions shown in FIG. 2; the runs were carried out with pure butene-1 and a spiked feed (isobutane and 5 mol % butene-1). The results are shown in FIG. 2. As can be seen, the effluent composition is substantially unchanged. Therefore the reformer can be used to convert the recycled butene-1 into butene-2 and prevent a build-up of butene-1.

Reasonable variations and modifications which will become apparent to those skilled in the art can be made from this invention without departing from the spirit and scope thereof.

What is claimed is:

1. Process to produce methyl-tert-butyl-ether by reacting isobutene and methanol in an ether forming zone in the presence of a catalyst under ether forming conditions which process comprises
   (a) passing an isobutane containing stream and steam into contact with a reforming catalyst comprising a catalyst base and a Group VIII metal in an isomerization and reforming zone at a temperature in the range of 950° F. to 1150° F. to convert at least some of the isobutane to isobutene,
   (b) withdrawing a reaction effluent from said isomerization and reforming zone,
   (c) passing at least a portion of said reaction effluent into an ether forming zone and reacting therein isobutene with methanol in the presence of an ether forming catalyst to form an methyl-tert-butyl-ether,
   (d) withdrawing methyl-tert-butyl-ether containing effluent from said ether forming zone and passing said effluent to a separation zone,
   (e) separating in said separation zone said ether containing effluent into
      (aa) a methyl-tert-butyl-ether containing product stream
      (bb) a 1-butene containing stream, and
      (cc) a 2-butene containing byproduct stream,
   (f) passing said 1-butene containing stream into said isomerization and reforming zone and into contact with said reforming catalyst such as to convert at least a portion of said 1-butene in said 1-butene containing stream and form 2-butene which is withdrawn from the separation zone as the by-product stream.

2. Process in accordance with claim 1 wherein the mole ratio of 1-butene to isobutane in said isomerization and reforming zone is in the range of 1/10 to 1/10000.

3. Process in accordance with claim 1 wherein the catalyst base comprises a zinc aluminate spinel, wherein the Group VIII metal comprises platinum in an amount of about 0.1 to about 5 parts by weight per 100 parts of weight of the catalyst base, and wherein the reforming catalyst further comprises tin in an amount of 0.1 to 1 parts by weight per 100 parts by weight of support.

* * * * *